(12) United States Patent
Bosio et al.

(10) Patent No.: US 6,830,886 B1
(45) Date of Patent: Dec. 14, 2004

(54) SUPPORTS FOR THE PARALLEL IDENTIFICATION AND TRANSCRIPTION PROFILING OF POLYNUCLEIC ACIDS

(75) Inventors: Andreas Bosio, Köln (DE); Wilhelm Stoffel, Köln (DE); Markus Stoffel, New York, NY (US)

(73) Assignee: Memorec Medical Molecular Research Cologne Stoffel GmbH, Cologne (DE)

( * ) Notice: Subject to any disclaimer, the term of this patent is extended or adjusted under 35 U.S.C. 154(b) by 0 days.

(21) Appl. No.: 09/701,584

(22) PCT Filed: Jun. 10, 1999

(86) PCT No.: PCT/EP99/04014

§ 371 (c)(1),
(2), (4) Date: Feb. 1, 2001

(87) PCT Pub. No.: WO99/64623

PCT Pub. Date: Dec. 16, 1999

(30) Foreign Application Priority Data

Jun. 10, 1998 (DE) .......................................... 198 25 899
Jun. 10, 1998 (EP) ............................................. 98110608

(51) Int. Cl.[7] .......................... C12Q 1/68; C12P 19/34
(52) U.S. Cl. ....................... 435/6; 435/91.2; 435/287.2; 422/104
(58) Field of Search ................................ 435/6; 514/44

(56) References Cited

U.S. PATENT DOCUMENTS

| | | | | |
|---|---|---|---|---|
| 4,695,392 A | * | 9/1987 | Whitehead et al. ....... | 252/62.54 |
| 5,474,895 A | * | 12/1995 | Ishii et al. ..................... | 435/6 |
| 5,543,296 A | * | 8/1996 | Sobol et al. ................... | 435/6 |
| 5,622,826 A | * | 4/1997 | Varma ........................... | 435/6 |
| 5,683,875 A | * | 11/1997 | Lichtenwalter ................ | 435/6 |
| 5,688,642 A | * | 11/1997 | Chrisey et al. ................ | 435/6 |

OTHER PUBLICATIONS

Guo Z, et al., "Direct Fluorescence Analysis of Genetic polymorphisms by Hybridization With Oligonucleotide Arrays on Glass Support", Nucleic Acid Research, vol.22, No. 24, 1994, 5456–5465.*
Schena M., "Genome Analysis With Gene Expression Microarrays", vol. 18, No. 5, 1996, 427–431.*
Zhen Guo et al., "Direct Fluorescence Analysis of Genetic Polymorphisms by Hybridication with Oligonucleotide Arrays on Glass Supports", vol. 22, No. 24, pp. 5456–5465 (1994).
Mark Schena, "Genome Analysis with Gene Expression Microarrays", vol. 18, No. 5, pp. 427–431 (1996).

* cited by examiner

Primary Examiner—Kenneth R. Horlick
(74) Attorney, Agent, or Firm—Jacobson Holman

(57) ABSTRACT

The invention relates to a support. Oligonucleotides or polynucleotides are covalently bound with the 5'- or 3'-termination on least one main surface of said support via bifunctional spacers and bifunctional linkers. The support is characterized in that the oligonucleotides or polynucleotides which are covalently bound with the 5'- or 3'-termination via bifunctional spacers and bifunctional linkers comprise 200 to 600 bp, and the oligonucleotides or polynucleotides can be obtained by using a method which comprises the following steps: Selecting homologous regions of mRNA of a target species and of at least one model species; selecting amplification primers which permit the amplification of 200 to 600, preferably 200 to 400 bp long nucleic acids from the homologous regions of both the mRNA of the target species and the mRNA of at least one model species, whereby the amplification primers optionally comprise a maximum of 1 mismatch per 6 nucleic acids of the amplification primer; immobilizing the nucleic acids on at the least one main surface of the support, said nucleic acids being obtained from the corresponding 200 to 600 bp long nucleic acids which are amplified for the target species or for the at least one model species by amplifications using the amplification primers.

16 Claims, 7 Drawing Sheets

Figure 1:
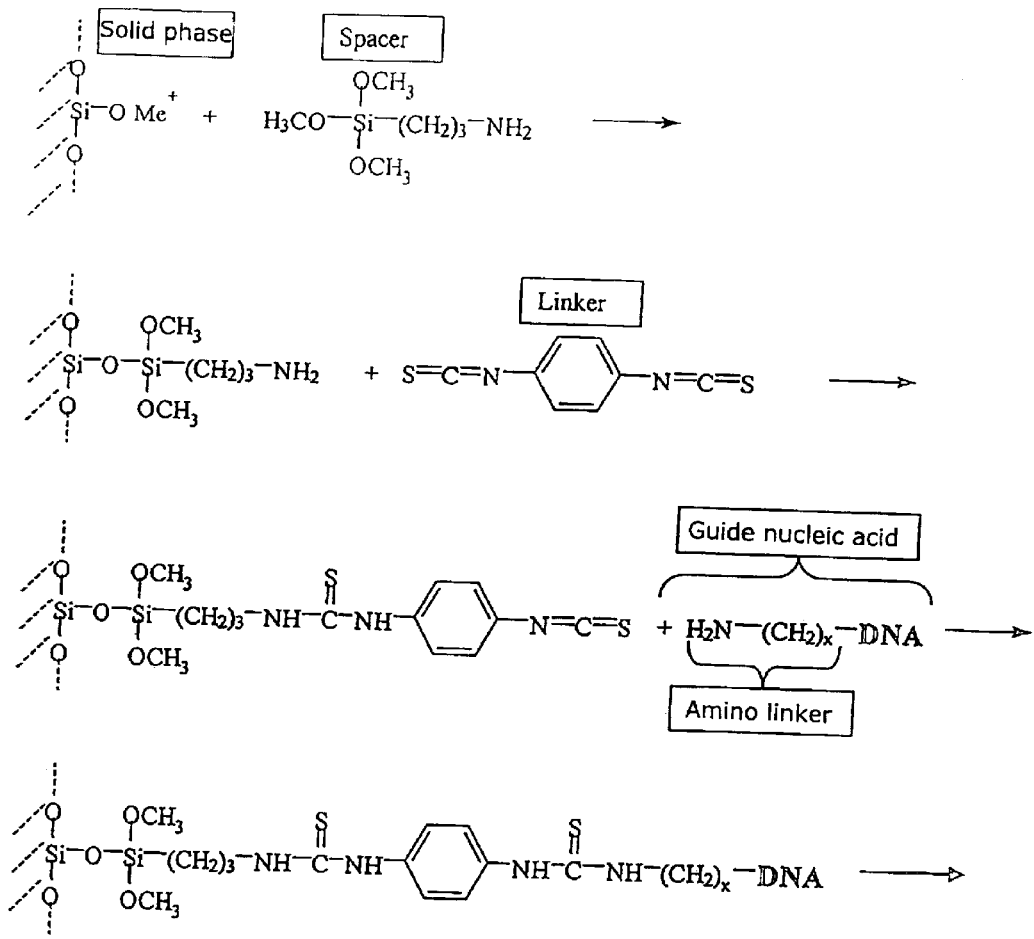

SUPPORTS FOR THE PARALLEL IDENTIFICATION AND TRANSCRIPTION PROFILING OF POLYNUCLEIC ACIDS

The present invention relates to a support comprising oligo- or polynucleotides covalently linked at their 5'- or 3'-termini to at least one major surface of said support through bifunctional spacers and bifunctional linkers, the use of the support according to the invention, the preparation of the support according to the invention, and a method for establishing transcription profiles.

Analyses performed on a molecular-biological level are increasingly gaining importance. In most cases, a mixture of nucleic acids to be analyzed is hybridized with so-called probes and characterized in such methods. Especially for problems in which a large number of polynucleic acids of different kinds are to be detected simultaneously, there are bottlenecks in the method. It is attempted to perform a large number of analytical steps within a short period of time, especially by a parallel operation of the process. There is often a problem in that support systems on which the hybridization experiments can be performed have a limited space capacity. Therefore, it is attempted to solve these problems by using supports on which a large number of samples can be placed. In particular, the prior art describes supports which have micrometer or nanometer compartments for receiving correspondingly small volumes of the analytes which are mostly in solution. Appropriate support systems can be obtained, for example, by etching the surfaces of wafers made of silicon.

E. M. Southern (E. M. Southern et al. (1992), Nucleic Acids Research 20: 1679 to 1684, and E. M. Southern et al. (1997), Nucleic Acids Research 25: 1155 to 1161) describes the preparation of so-called oligonucleotide arrangements by direct synthesis on a glass surface derivatized with 3-glycidoxypropyltrimethoxysilane and then with a glycol.

The publication by S. P. A. Fodor (A. C. Pease et al. (1994), Proc. Natl. Acad. Sci. USA 91: 5022 to 5026) relates to a similar method. The in situ oligonucleotide synthesis described therein is performed by fully automated light-controlled combinatorial chemistry. The direct synthesis of oligonucleotides on a glass support allows a maximum length of about 30 bases. Ensuring a correct course of the synthesis for an individual sequence of longer oligonucleotides, if at all possible, involves an expenditure which is no longer justifiable. As a guide DNA, these oligonucleotides allow the hybridization of only a rather short length of the analyte nucleic acid. To circumvent this drawback, several oligonucleotides are synthesized as guide DNAs for each nucleic acid to be analyzed. This results in higher demands for space and thus a larger sample volume of the analyte nucleic acid. Further, the small length of the oligonucleotides does not preclude cross hybridizations with different analyte nucleic acids. This makes an unambiguous assignment of the recorded signals difficult.

For the preparation of so-called DNA chips, P. O. Brown (DeRisi et al. (1997), Science 278: 680–686) discloses polylysine-coated glass surfaces to which minute DNA quantities are applied dropwise by capillary techniques. However, the immobilization of the guide DNA on a polylysine surface adversely affects hybridization and thus considerably increases the detection limit and reduces the reliability in the detection of the analyte nucleic acids.

L. M. Smith (Z. Guo et al. (1994), Nucleic Acids Research 22: 5456–5465) describes a technology for the immobilization of oligonucleotides in which oligonucleotides are derivatized with a 5'-terminal amino group and then applied to a glass surface derivatized with 3-aminopropyltrimethoxysilane and then with 1,4-phenyldiisothiocyanate. While the chemistry used for the immobilization of the oligonucleotides avoids the drawbacks of the previously described systems, there are still the previously mentioned drawbacks caused by the use of short oligonucleotides as the guide DNA.

Such systems can be prepared only with a high expenditure usually, and often fail to reach a satisfactory capacity of sample compartments which would be necessary for appropriate parallelization.

In addition, the use of complete cDNAs is not advisable. On the one hand, cross-reactions will occur in highly homologous gene families, and on the other hand, the cDNAs contain repetitive elements which may result in non-specific hybridizations. This may result in artifacts. In comparisons between different species, the mentioned artifacts may result in a severe limitation of the method.

Thus, it has been the object of the present invention to provide a support which avoids the mentioned drawbacks of the prior art. In particular, the support according to the invention should be able to bind nucleic acids, preferably having a defined sequence and, if possible, the same length, in high densities and allow a high level of parallelization of samples to be examined.

According to the invention, this object is achieved by a support having the features of claim 1. Preferred embodiments of the support according to the invention are found in the dependent claims. The present invention also relates to a method for the preparation of the support according to the invention and its use. The provision of the support according to the invention enables a novel and inventive method which advantageously enables the quantification of transcription profiles.

FIG. 1 shows a reaction scheme in which the chemical derivatization of the solid phase surface and coupling of the guide DNA are illustrated.

Figure 2B:
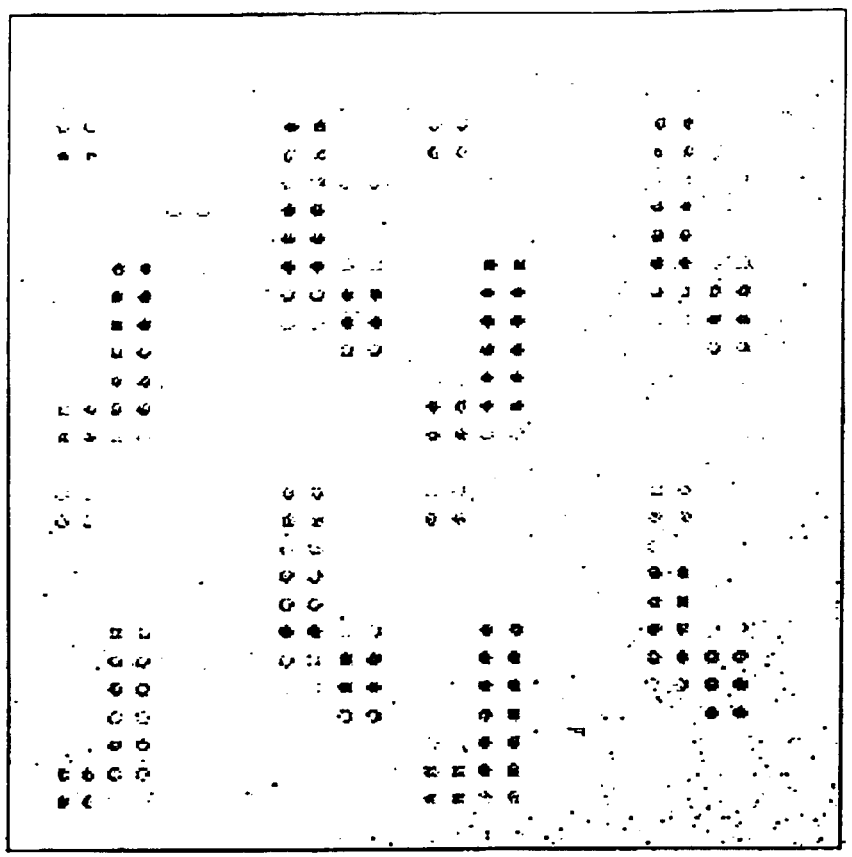
Figure 2A:
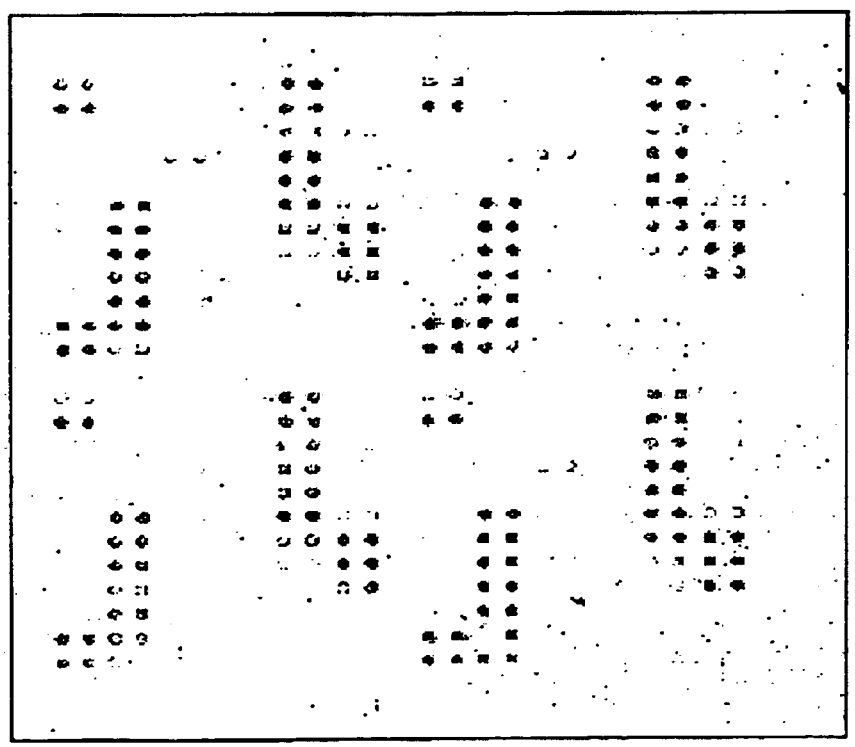

FIG. 2 shows a comparison of the expression levels of 72 different genes in two similar, but differently labeled wild type mouse brain RNA samples, FIG. 2a relating to a sample labeled with Cy3-dCTP and FIG. 2b relating to one labeled with Cy5-dCTP. FIG. 2c shows signal intensities wt/wt of the two fluorescence-labeled samples in a double-logarithmic dot diagram. FIG. 2d shows the expression quotient wt/wt, the ratio of Cy3-labeled to Cy5-labeled sample being illustrated as a semilogarithmic bar diagram.

FIG. 3 shows a comparison of the expression levels of 72 different genes in a wild type mouse brain RNA sample and a mutant (PLP$^{-/-}$ MBP$^{-/-}$) mouse brain RNA sample. FIG. 3a relates to the expression profiles obtained with Cy3-dCTP-labeled nucleic acids, and FIG. 3b shows the expression profiles obtained with Cy5-dCTP-labeled nucleic acids. FIG. 3c shows the corresponding signal intensities as in FIG. 2c. FIG. 3d shows normalized expression quotients wt as in FIG. 2d.

The support according to the invention comprising oligo- or polynucleic acids covalently linked to at least one major surface of the substantially planar support has a reactive group on the major surface of the support, which reactive group has reacted with a bifunctional spacer to form a covalent bond between a functional group of the spacer and the reactive group of the major surface of the support. "Major surface" means any surface which has a sufficient dimension to receive a number of samples necessary for the use of the support.

The second functional group of the bifunctional spacer has reacted with a functional group of a bifunctional linker, and the second functional group of the bifunctional linker has reacted with the oligo- or polynucleotide to be covalently linked (guide nucleic acid) to form a covalent bond at the 5'- or 3'-terminus of said oligo- or polynucleotide.

The support according to the invention is characterized in that said oligo- or polynucleic acids covalently linked at their 5'- or 3'-termini through bifunctional spacers and bifunctional linkers have a length of from 200 to 600 bp. The oligo- or polynucleic acids can be obtained by a method comprising the following steps:

selection of homologous regions of mRNA from a target species and at least one model species;

selection of amplification primers allowing the amplification of nucleic acids having a length of from 200 to 600 bp, preferably from 200 to 400 bp, from the homologous regions of both the mRNA from said target species and the mRNA from said at least one model species, the amplification primers optionally having a maximum of 1 mismatch per 6 nucleic acids of the amplification primer;

on said at least one major surface of the support, immobilization of the nucleic acids obtained by amplifications of corresponding nucleic acids having a length of from 200 to 600 bp for said target species or said at least one model species using the amplification primers.

Preferably, the polynucleotide is an RNA, DNA or PNA. The support preferably consists of a glass or another material mainly consisting of silica. Preferably, said bifunctional spacer bonded to the major surface of the support according to the invention has the following structure:

(XO)$_3$—Si—Y—Nu, wherein
X=$C_1$–$C_3$ alkyl,
Y=$C_2$–$C_4$ alkylene,
Nu=a nucleophilic group such as —NH$_2$, —NHR, with R=—CH$_2$—CH$_2$—NH$_2$, —CH$_2$—CH$_2$—NH—CH$_2$—CH$_2$—NH$_2$, —CO—NH$_2$ or SH.

Particularly preferred is a spacer having the structure

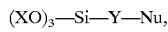
Me$_3$OS$_1$—CH$_2$—CH$_2$—CH$_2$—NH$_2$.

Preferably, said bifunctional linker is selected from the group of rigid homobifunctional linkers consisting of:

2,7-substituted fluorene, 2,6-substituted naphthalene, 2,6-substituted anthracene, 2,7-substituted phenanthrene, 4,4'-substituted biphenyl, 4,4'-substituted benzoin (C$_6$H$_5$—CO—CH(OH)—C$_6$H$_5$), 4,4'-substituted benzil (C$_6$H$_5$—CO—CO—C$_6$H$_5$), 4,4'-substituted benzophenone (C$_6$H$_5$—CO—C$_6$H$_5$), 4,4'-substituted diphenylmethane (C$_6$H$_5$—CH$_2$—C$_6$H$_5$), 4,4'-substituted stilbene (C$_6$H$_5$—CH=CH—C$_6$H$_5$), 1,3-substituted allene (CH$_2$=C=CH$_2$), 1,4-disubstituted benzene.

Especially preferred is a linker having the following structure:

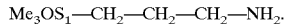
S=C=N-phenylene-N=C=S.

The use of rigid bifunctional linkers has the advantage that substantially only one of the two groups reacts with the surface of the support.

As functional groups with which said homobifunctional linker is substituted, there are preferred:

aldehydes and ketones, isocyanates, isothiocyanates, carboxylic acids, carboxylic acid derivatives:

a) carboxylic acid esters: generally the readily available methyl and ethyl esters. However, activated esters, such as esters of p-nitrophenol or N-hydroxysuccinimide, should be more suitable;

b) carboxylic acid chlorides (R—COCl);

c) carboxylic acid azides (R—CON$_3$);

d) mixed anhydrides with carbonic acid monoester (R—CO—O—COR').

The support according to the invention preferably has an oligo- or polynucleotide covalently bonded to said bifunctional linker, said covalent bonding being effected through a primary amino group attached, synthetically or by a PCR reaction, on the 3'- or 5'-terminus through an alkane having a length of from 4 to 30 methylene groups or through a polyether with from 2 to 20 repeating units.

DNA fragments having a length of from 200 to 400 bp are preferred guide DNAs for the following reasons: The length and the thus determined melting temperature are sufficient to ensure non-redundant hybridization with a high reliability for a careful selection and maximum complexity as exhibited by the human genome.

The shortest cDNAs known are in a range of about 200 bp. Thus, all cDNAs of a cDNA population to be analyzed can be bound to the solid phase completely or as fragments of 200 to 400 bp. In the hybridization with a labeled analyte nucleic acid, the similar length of all DNAs applied results in hybridization signals which are not adversely affected by the length or different hybridization kinetics of the guide nucleic acid.

The sequences of the guide DNAs to be applied are preferably searched individually, e.g., using a software prepared expressly for that purpose, especially in the publicly available gene data bases. Preferably, the guide DNA is to be tested for non-redundancy. Thus, it is essentially excluded that a guide DNA will hybridize with several analyte nucleic acids and thus can result in false positive signals. The guide DNA is amplified from total RNA according to common protocols, e.g., using RT-PCR and sequence-specific primers.

The sequence-specific primers are preferably selected to be suitable for the amplification of the desired guide nucleic acid from different species, such as human and murine. In this process too, a length of the guide nucleic acid of from 200 to 400 bp has proven useful. The length is sufficient to define primers having a length of from 18 to 22 bp in about 70 to 80% of the instances, which primers allow the amplification of the guide nucleic acid of both species with a maximum of 3 mismatch bases.

As the support, per se known glass microscope slides are preferably employed. In contrast to nylon membranes which are often used, slides have an advantage, for example, in that they are substantially more easily processed and subsequently washed free from non-specific hybridization signals due to their rigidity and the fact that glass is inert towards most reagents. Further, a great advantage resides in the fact that glass can be used for fluorescence-based analysis.

Especially the use of piezoelectric nanodispensers for applying the guide DNA to the solid phase enables very exact dosage, which is preferred for a reliable quantification of the analyte DNA, and the latter is directly related with a reproducible amount of guide DNA. The possibility of applying drop volumes of 0.1 nl allows to arrange 100,000 different guide DNAs on the surface of a slide (76×26 mm), for example. Thus, it becomes possible to detect very small quantities of nucleic acids.

The immobilization of the guide DNA according to the invention through the reaction of an isothiocyanate with a primary amine to yield N-substituted thioureas is advantageous. Both the chemicals and the amino-modified 5'-oligonucleotide primers for the synthesis of DNAs are inexpensive as compared with other synthetic methods which are based on phosphoramidite chemistry. N-substituted thioureas provide stable bonding. The DNAS covalently linked by the method herein described are not separated from the solid phase even by several hours of boiling in water. Thus, the DNA chips may also be accessible to repeated use. With other chips, this is not possible because, inter alia, the washing conditions for removing specific and non-specific analyte DNAs as required for regeneration cannot be selected stringent enough due to the instability of the solid phase bonding.

The specific bonding of the DNA through its 5'-end or 3'-end substantially ensures that almost the whole guide DNA is available for hybridizing with the analyte DNA and is not adversely affected by non-specific binding to the surface. Due to its rather rigid structure and negative charge, the DNA double helix will become aligned perpendicular to the solid phase and thus enable a maximum density of guide DNA to be applied.

The specific and monovalent binding of the guide DNA to the solid phase not least allows to control the quantity of DNA applied via the derivatized isothiocyanate groups available.

The present invention also relates to the use according to the invention of a support according to the invention in a method for identifying and quantifying (assaying) polynucleotides by labeling the polynucleotides to be analyzed and subsequently hybridizing them on the support.

The method according to the invention for establishing transcription profiles comprises the following steps:

homologous regions of mRNA from a target species and at least one model species are selected;

amplification primers allowing the amplification of nucleic acids having a length of from 200 to 600 bp, preferably from 200 to 400 bp, from the homologous regions of both the mRNA from said target species and the mRNA from said at least one model species are selected, the amplification primers having a maximum of 1 mismatch per 6 nucleic acids of the amplification primer;

corresponding nucleic acids having a length of from 200 to 600 bp for said target species or said at least one model species are amplified by amplifications using the amplification primers, and the nucleic acids obtained are immobilized on said at least one major surface of the support;

said at least one support is incubated with a DNA or RNA sample to be analyzed, and the quantity of bound DNA or RNA is determined.

To enable the establishing of a transcription profile, i.e., a qualitative and quantitative analysis of gene expression, the nucleic acid to be analyzed, e.g., RNA or DNA, is labeled. Then, due to the hybridization process, the cDNAs immobilized on the surface are joined with the corresponding labeled DNAs or RNAs of the sample to be analyzed. This results in the cDNAs on the surface of the support being labeled with the corresponding counterpart which has been present in the sample to be analyzed.

Said labeling of the sample to be analyzed can be effected by various methods.

For example:
1. agents directly reacting with the RNA or DNA may be used;
2. modified nucleotides can be added enzymatically;
3. the RNA can be transcribed into labeled cDNA by a RT reaction with incorporation of modified nucleotides.

The agents or modified nucleotides may contain elements which are, for example, radioactive or can be excited for fluorescence or luminescence, so that direct measurement is possible with a suitable detector device. However, they may also serve as linkers or haptenes to enable a subsequent coupling with a second labeled molecule.

By the use of different fluorescence signals, different samples to be analyzed may also be simultaneously applied to one support for hybridization so that a direct comparison of these different samples on one support is possible. Thus, for example, two different samples can be treated as follows. The nucleic acids present in one sample are labeled with a first fluorescent compound, and the nucleic acids present in the second separate sample are labeled with a second fluorescent compound whose emitted fluorescence is distinct from that of the first fluorescent compound.

In addition to the labeled samples, the hybridization solution contains salts, detergents and unlabeled DNA, so that optimum hybridization conditions matched to the respective support can be achieved. Prior to the actual hybridization, it may be appropriate to perform a so-called prehybridization.

Thus, the corresponding support is incubated with the hybridization solution, but without a labeled sample; and the reaction conditions can be optimized.

After the hybridization reaction, non-specifically bound sample components are separated off by one or, preferably, more washing procedures. The washing solutions employed contain, in particular, detergents, such as sodium dodecylsulfate, and low amounts of salts. The washing procedure(s) are usually performed in a temperature range of from 20 to 60° C. and over a period of from 5 to 20 minutes.

To establish a transcription profile, the signals recorded by means of a suitable detector device are quantified. For example, the signal intensity directly corresponds to the number of labeled molecules present in the hybridization solution and thus to the expression level of the respective gene in the sample examined. By normalizing these values to an internal or external standard, transcription profiles of different samples can be compared with each other.

The detection of the hybridization of guide and analyte nucleic acids can be effected by various methods. One suitable method involves the labeling of the analyte nucleic acid with fluorescent nucleotides, followed by detection of the hybridization by fluorescence microscopy. For the differential or relative quantification of analyte nucleic acids, a known quantity of reference nucleic acid carrying a second fluorescence marker is added to the fluorescence-labeled analyte nucleic acid and applied to the immobilized guide DNA for hybridization. A relative quantification of the analyte nucleic acid is effected by comparing the detected signal intensities.

The method according to the invention for the preparation of a support according to the invention comprises the following steps.

The bifunctional spacer in a polar aprotic solvent is applied to the major surface of the support, and any excess (unreacted) spacer is subsequently removed. The bifunctional spacer is applied to the major surface of the support, for example, in a 95% by volume acetone/water mixture. After the optional washing steps, the support is preferably dried, especially by heating.

The bifunctional linker is dissolved in an essentially anhydrous polar aprotic solvent and reacted with the spacer bound to the major surface. The linker should preferably be present in a low concentration, for example, at around 0.5% by weight, in the polar aprotic solvent. In this case, a solvent system with 10% pyridine/dimethylformamide (% by volume) may be used, for example. The reaction time depends on the reactivity of the bifunctional spacer or bifunctional linker and may be as long as several hours at room temperature or increased temperature. In this state, the support can be cooled and stored in a dry place for several months.

In a further reaction step, the oligo- or polynucleotide modified with an amino group at its 5'- or 3'-terminus through an alkylene group is taken up in a buffer. In particular, a basic buffer, for example, a carbonate buffer, may be conveniently employed. The mixture is incubated on the previously prepared support for binding the oligo- or polynucleotide to a free group of the bifunctional linker. This may be done, in particular, for a period of several hours in a vapor-saturated atmosphere. Thereafter, any unreacted groups of the bifunctional linker are removed. In particular, amines, such as ethanolamine or hydroxylamine, are used for this purpose. These are typical blocking reactions for reactive groups per se known to those skilled in the art.

Thereafter, the oligo- or polynucleotide bound to the support is denatured. For denaturing, for example, the support is boiled in bidistilled water together with the covalently bound polynucleotide. To maintain the denatured state, the support may be washed with pure alcohol and then stored in a cool and dry place.

The invention is described in more detail by the following further explanations.

FIG. 1: Chemical derivatization of the solid phase surface and covalent coupling of the guide DNA.

Cleaning of the glass slides: 76×26 mm, clear white glass, no coating, frosted edge or marking area; e.g., Fisher Scientific under the designation "Glass microscope slides, clear white, with cut edges": agitating the slides for two hours in a solution of 2 N NaOH in 70% EtOH, three washes with completely desalted (and bidistilled) water and one wash with acetone.

Coating: The slides are immersed in a 1% solution of 3-aminopropyltrimethoxysilane (APTMS) in 95% acetone/water for two minutes, followed by ten washes in acetone for five minutes each and drying at 110° C. for 45 minutes.

Derivatization of the coated slides with a linker: The slides are immersed in a solution of 0.2% by weight 1,4-phenyldiisothiocyanate (PDC)/10% by volume pyridine/dimethylformamide for two hours and subsequently washed with methanol and acetone.

Application of the guide DNA for covalent coupilng: 0.1 nl volumes of PCR fragments are applied to defined positions on the slides using a nanodispenser, the slides are incubated at 37° C. in a moist atmosphere for at least one hour, followed by one rinse with 1% $NH_4OH$ and three rinses with water, cooling and storing in a dry place.

For separating the DNA complementary strand from the template strand, the slides are incubated at 96° C. in completely desalted water for ten minutes, rinsed with 96% ethanol and subsequently dried at room temperature. The slides are now ready for hybridization with the analyte nucleic acid.

According to the invention, the following procedure may also be used.

A glass surface which has not been processed for use as a microscope slide may be employed.

The density of the derivatizable amino groups on the glass surface can be varied between 0.1 and 10% through the concentration of the APTMS solution, whereby different densities of coupled guide DNA can be adjusted.

The density of the derivatizable amino groups can further be controlled by a mixture of APTMS/propyltrimethoxysilane (PTMS) or APTMS/tetramethoxysilane (TeMS) in a ratio of from 1:10 to 10:1.

Prior to the derivatization of the amino groups with PDC, the bound APTMS molecules can be cross-linked: 30 minutes at 90° C. with 5% APTMS or PTMS or TeMS in water; pH 5.5 to 5.8.

As described above for APTMS, the concentration of PDC can be varied between 0.04% and 1% to thereby adjust the density of the linkers for receiving the guide DNA according to need.

Instead of PDC, other molecules substituted with diisocyanates can also be used. PDC and other rigid homobifunctional linkers have the advantage that the cross-linking of neighboring amino groups is sterically hindered. In order to obtain a larger distance between the support surface and the DNA, it may be advantageous to insert longer linker molecules between the derivatized surface and the DNA or to use a chain of several units of short linker molecules.

The generation of the PCR fragments is preferably effected by transcription of the information of an mRNA into DNA using reverse transcriptases. This DNA is then amplified by polymerase chain reaction (PCR). For both enzymatic processes, oligonucleotide primers which will hybridize to a template and serve as synthesis initiators for the respective polymerase are required, inter alia.

A list of genes is established whose parallel identification and quantification is of interest. This list is used as an input for a program created for this purpose. By means of the program, the sequences of the genes to be analyzed are taken from, for example, a publicly accessible gene data base, and oligonucleotide pairs are designed which give each a specific amplification of 200 to 400 bp fragments from each gene. The oligonucleotides are synthesized, and the RT PCR is performed according to a protocol per se known to those skilled in the art. For separating non-incorporated nucleotides and oligonucleotides, the PCR fragments are precipitated with ethanol, and a concentration of 10 to 1000 ng/$\mu$l, preferably 50 to 500 ng/$\mu$l, is adjusted with 100 mM sodium carbonate/sodium hydrogencarbonate solution, pH 9.

In the following two Examples relating to the establishing of a transcription profile, supports were prepared by the method according to the invention. Seventy-two different murine cDNAs were generated using the corresponding specific primers (oligonucleotides) in an RT PCR from murine brain total RNA, applied to the derivatized glass surface and covalently bound. Each cDNA was applied twice each in four quadrants, i.e., a total of eight times. Two nanoliters each of the corresponding cDNA having a concentration of 100 ng/$\mu$l was applied using a dispensing automatic. The diameter of the dried-on samples was 350 $\mu$m each, and the distance from one center to the next for two neighboring samples was 0.750 $\mu$m.

In the Examples, an expression profile of wild type and mutant mouse brain samples is established. Thus, the brain of 18-day-old wild type and mutant mice ($MBP^{-/-}/PLP^{-/-}$) was dissected, and the total RNA extracted. For labeling the respective samples, the mRNA was isolated from 100 $\mu$g each of total RNA and transcribed into the corresponding cDNA using a reverse transcriptase. During this process, fluorescence-labeled nucleotides (Cy3-dCTP or Cy5-dCTP) were incorporated. The labeled samples were purified, adjusted to the optimum conditions for hybridization and concentrated to a volume of 20 $\mu$l.

Prior to the actual hybridization reaction, the support was subjected to prehybridization. Thus, 20 $\mu$l of a salt/detergents/unlabeled DNA solution was applied to the support and provided with a cover slip. After two hours of incubation at 62° C. in a moist chamber sealed towards the exterior, the reaction solution was cooled to 20° C., the cover slip was removed, and a 20 µl drop of the actual hybridization solution was added. Again, the solution was provided with a cover slip and incubated at 62° C. in the mentioned chamber for 12 hours. Subsequently, non-specifically bound samples were washed off the support with two different washing solutions. The detection of the signals was effected using the laser scanning device "ScanArray 3000" supplied by General Scanning, Watertown, Mass., USA. Commercially available software ("ImaGene" of BioDiscovery, Inc., Los Angeles, Calif., USA) was used for evaluating the signals.

EXAMPLE 1 mRNA was isolated twice from the same total RNA and labeled with Cy-3-dCTP or Cy5-dCTP. Both samples were applied to a support for hybridization as described above. FIG. 2 shows the images recorded for the Cy3-labeled sample (a) and for the Cy5-labeled sample (b).

Figure 2C:
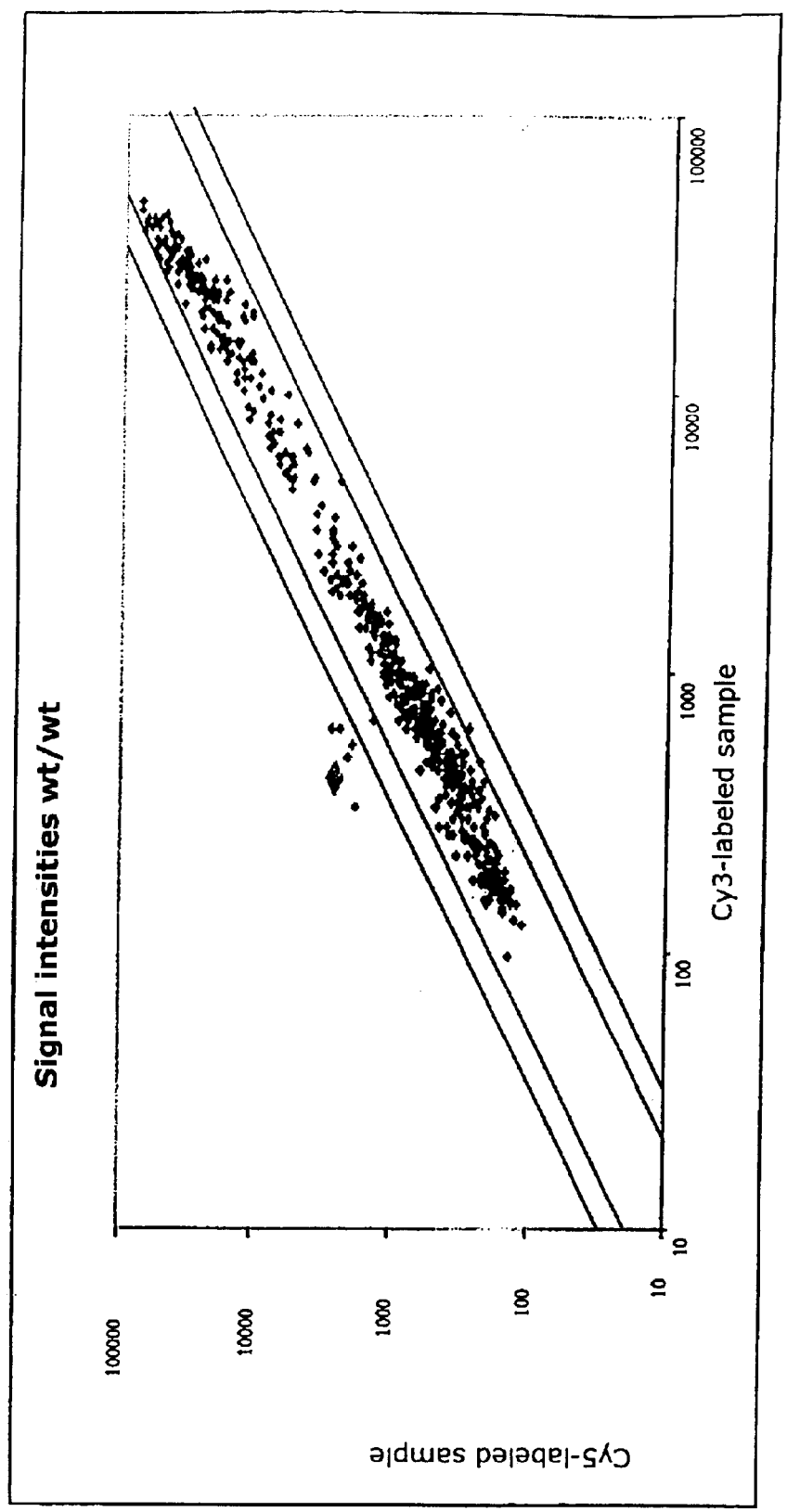
Figure 2D:
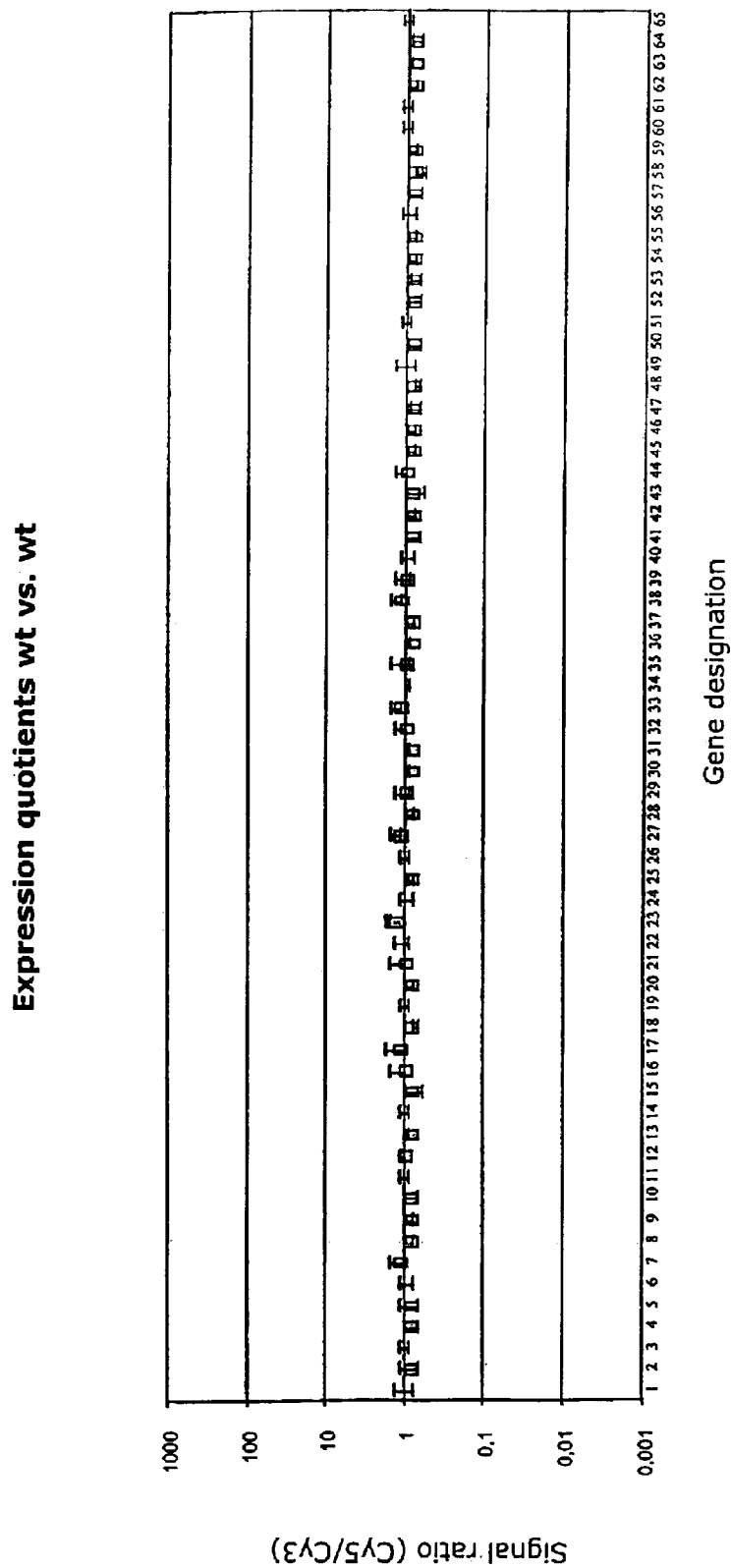

The signal intensity values from the two fluorescence-labeled samples as obtained using the ImaGene software are represented in FIG. 2c in a double-logarithmic dot diagram. Each dot in the diagram represents one cDNA applied to the support. Since each of the 72 cDNAs was applied eight times, eight dots are obtained for each cDNA. On the x and y axes, the signal intensities for the Cy3-labeled and Cy5-labeled samples, respectively, can be read for the respective cDNA. The solid line encloses all dots whose Cy3 and Cy5 signal intensities differ by no more than a factor of 2. The dotted line forms the boundary for a three-times differential signal intensity. Since the two labeled samples are derived from the same total RNA, all dots are enclosed by the solid line. The absolute intensity of the individual dots and thus ultimately the expression level of the corresponding genes extends through three powers of ten. FIG. 2d shows the ratio of Cy3 to Cy5 of the labeled sample as a semilogarithmic bar diagram. The data are respectively based on the mean values from the eightfold applied cDNAs.

Figure 3B:
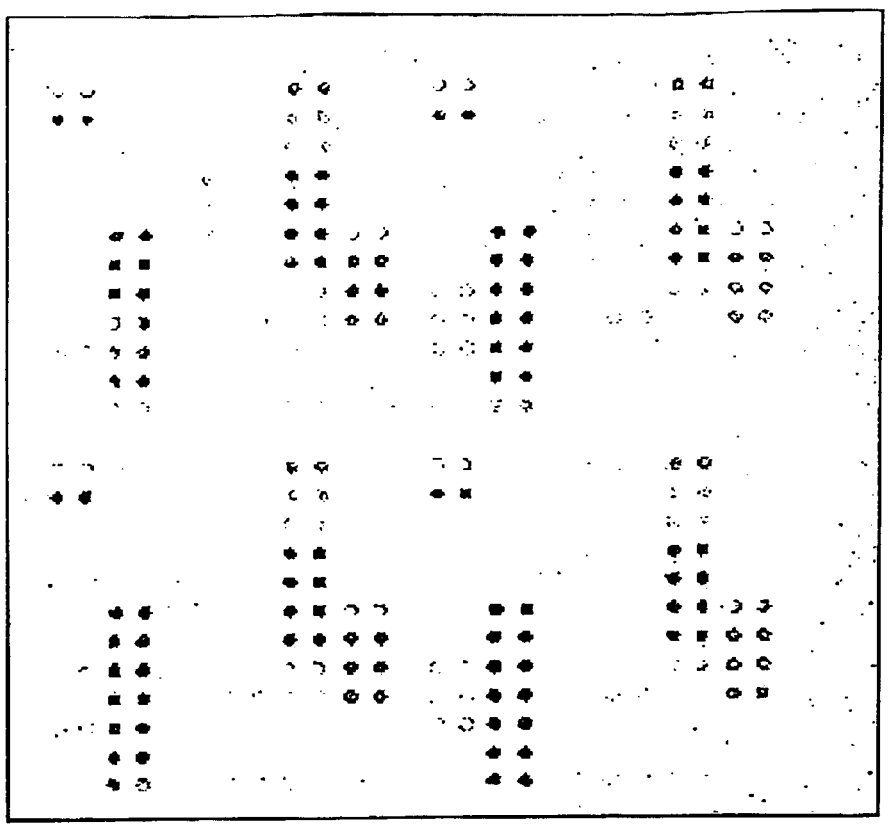
Figure 3A:
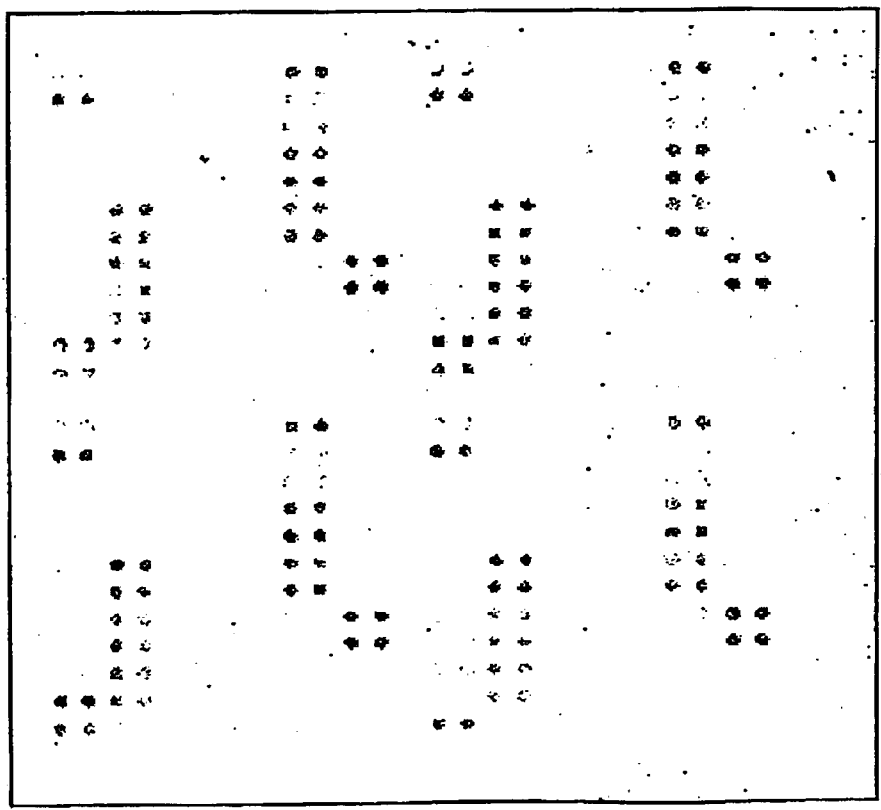
Figure 3C:
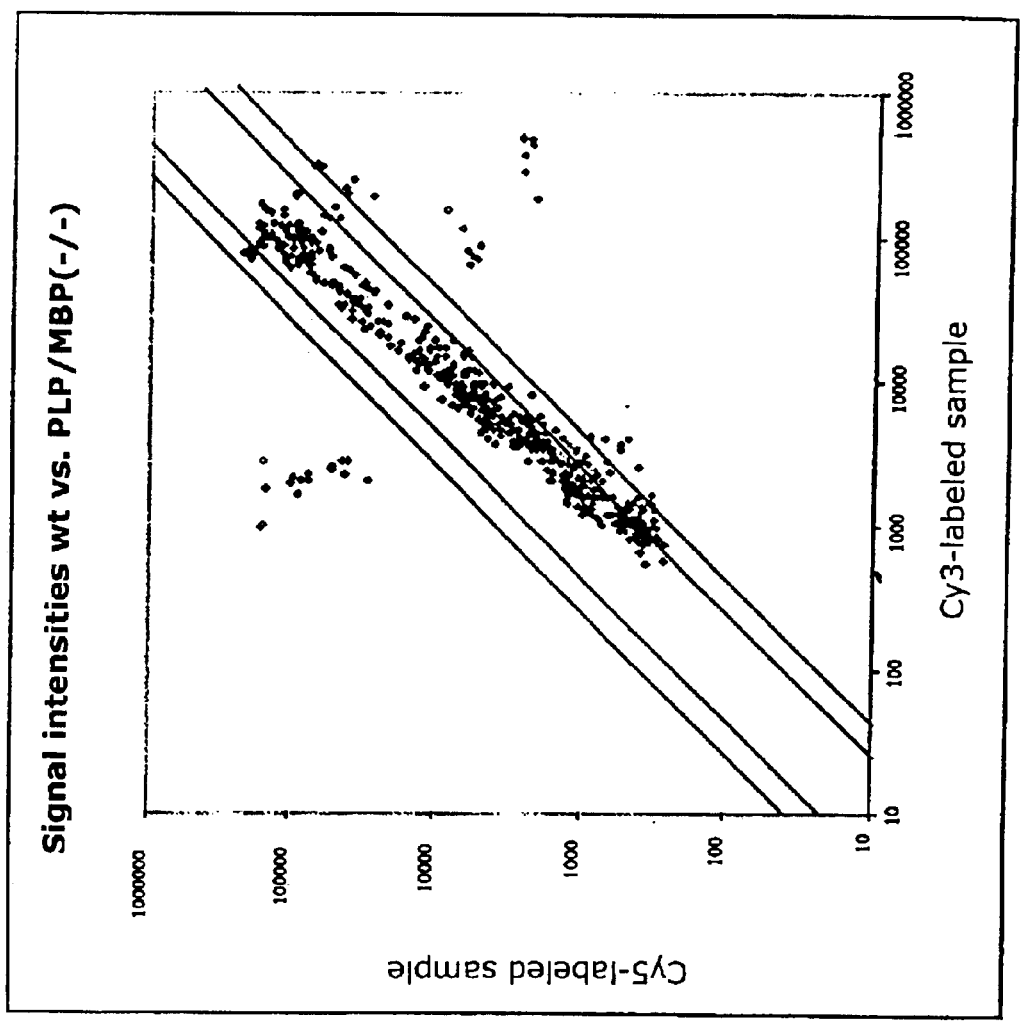
Figure 3D:
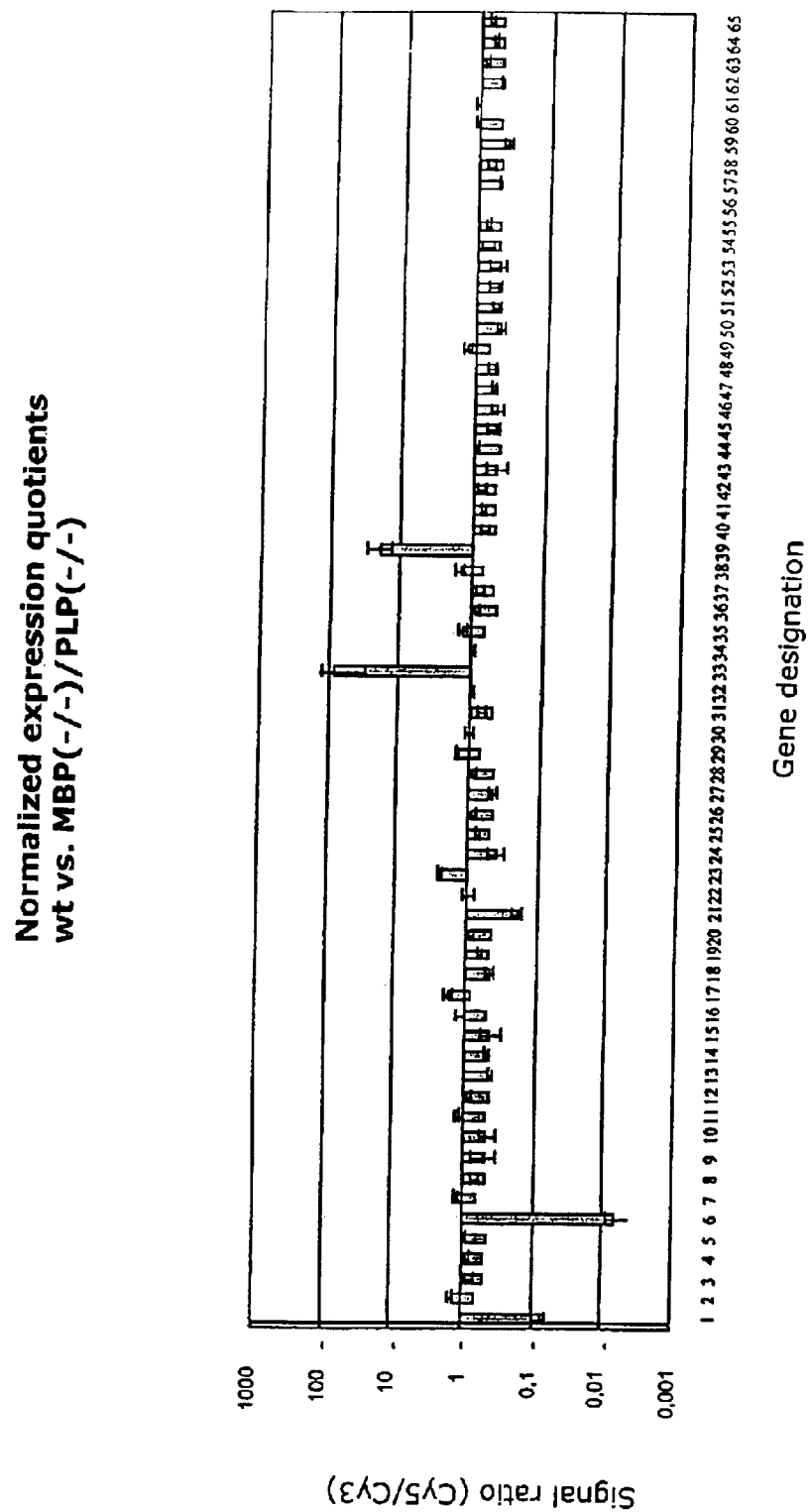

EXAMPLE 2
Comparison of the Expression Pattern of a Wild Type Sample with that of a Mutant Sample The wild type sample was labeled with Cy3, and the mutant sample was labeled with Cy5. FIGS. 3a and b again show the recorded images. From FIG. 3c, it can be seen that many dots are outside the area bounded by the dotted lines. Thus, the corresponding genes are expressed on levels which differ by more than a factor of three. In FIG. 3d, the signal quotients of the mean values are plotted for each cDNA. Genes 1, 6, 33 and 39 show the highest differences in expression level. Thus, for example, gene No. 6 is expressed at an about 100 times higher level in the wild type sample while gene No. 33, for example, is expressed at an about 100 times higher level in the mutant sample. The sum of the cDNAs detectable in this analysis and the related expression levels can be defined as a transcription profile for the respective sample. The differential expression of some genes as demonstrated in this analysis can be considered a first indication of a causal relation between these genes and the genes mutated in the mutant sample.

What is claimed is:

1. A support comprising polynucleotides covalently linked at their 5'- or 3'-termini to at least one major surface of said support through at least one bifunctional spacer and at least one bifunctional linker, wherein:
said polynucleotides have a length of from 200 to 600 bp;
said bifunctional linker is selected from the group of rigid homobifunctional linkers consisting of
1,4-disubstituted benzene, 2,7-substituted fluorene, 2,6-substituted naphthalene, 2,6-substituted anthracene, 2,7-substituted phenanthrene, 4,4'-substituted biphenyl, 4,4'-substituted benzoin ($C_6H_5$—CO—CH—(OH)—$C_6H_5$), 4,4'-substituted benzil ($C_6H_5$—CO—CO—$C_6H_5$), 4,4'-substituted benzophenone ($C_6H_5$), 4,4'-substituted diphenylmethane ($C_6H_5$—$CH_2$—$C_6H_5$), 4,4'-substituted stilbene ($C_6H_5$—CH=CH—$C_6H_5$), and 1,3-substituted allene ($CH_2$=C=$CH_2$);
said polynucleotides are covalently bound to a functional group of said bifunctional linker through a primary amino group attached, on the 3-' or 5'-terminus through an alkane having a length of from 6 to 18 methylene groups or though a polyether having from 2 to 20 repeating units; and
the polynucleotides are prepared by amplification.

2. The support according to claim 1, wherein said polynucleotide is RNA, DNA or PNA.

3. The support according to claim 1, wherein said support is made of glass or another material consisting essentially of silica.

4. The support according to claim 1, said bifunctional spacer having the structure

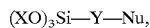

wherein
X=$C_1$–$C_3$ alkyl,
Y=$C_2$–$C_4$ alkylene, and
Nu=a nucleophilic group.

5. The support according to claim 4, wherein the nucleophilic group is —$NH_2$ or —NHR, with R=—$CH_2$—$CH_2$—$NH_2$, —$CH_2$—$CH_2$—NH—$CH_2$—$CH_2$—$NH_2$, —CO—$NH_2$, or SH.

6. The support according to claim 1, wherein said spacer is (MeO)$_3$Si—$CH_2$—$CH_2$—$CH_2$—$NH_2$.

7. The support according to claim 1, wherein said rigid homobifunctional linker comprises functional groups selected from the group consisting of:
aldehydes and ketones;
isocyanates and isothiocyanates;
carboxylic acids; and
carboxylic acid derivatives.

8. The support of claim 7, wherein the carboxylic acid derivatives are selected from the group consisting of:
a) carboxylic acid esters;
b) carboxylic acid chlorides (R—COCl);
c) carboxylic acid azides (R—CON$_3$); and
d) mixed anhydrides with carbonic acid monoester (R—CO—O—COR').

9. The support of claim 8, wherein the carboxylic acid esters are selected from the group consisting of methyl esters, ethyl esters, activated esters, and esters of p-nitrophenol and p-hydroxysuccinimide.

10. The support of claim 1 wherein the support does not comprise a polyT-spacer.

11. The support of claim 1 wherein the number of different polynucleotides is at least 72.

12. The support of claim 11, wherein the number of different polynucleotides is at least 439.

13. A method for identifying and quantifying polynucleotides comprising the steps of:

a) labeling the polynucleotides to be analyzed;

b) hybridizing the polynucleotides on the support according to claim 1; and c) detecting hybridized labeled nucleic acids;

wherein steps (a) and (b) are performed in any order.

14. A method for establishing transcription profiles comprising:

a) selecting homologous regions of mRNA from a target species and at least one model species;

b) selecting amplification primers from the homologous regions of both the mRNA from said target species and the mRNA from said at least one model species, wherein the amplification primers allow amplification of nucleic acids having a length of from 200 to 600 bp, and wherein each amplification primer has a maximum of 1 mismatch per 6 nucleic acids of the amplification primer;

c) amplifying, using the amplification primers, corresponding nucleic acids having a length of from 200 to 600 bp for said target species or said at least one model species;

d) immobilizing the nucleic acids obtained on at least one support according to claim 1;

e) incubating said at least one support with a DNA or RNA sample to be analyzed; and f) determining the quantity of bound DNA or RNA.

15. The method of claim 14, herein the nucleic acids have a length of 200 to 400 bp.

16. A method for generating of a support according to claim 1, comprising:

a) applying the spacer in a polar aprotic solvent to the major surface of the support;

b) removing excess unreacted spacer;

c) dissolving the linker in an anhydrous polar aprotic solvent wherein the linker and the spacer, bound to said major surface, react;

d) dissolving in a buffer the polynucleotides modified with an amino group at their 5'- or 3'-termini through an alkylene group;

e) incubating the polynucleotides on said support to react and bind the polynucleotides to free groups of bifunctional linkers;

f) optionally removing excess free groups of the bifunctional linkers; and g) denaturing the polynucleotides bound to the support.

* * * * *

UNITED STATES PATENT AND TRADEMARK OFFICE
CERTIFICATE OF CORRECTION

PATENT NO. : 6,830,886 B1
DATED : December 14, 2004
INVENTOR(S) : Bosio et al.

It is certified that error appears in the above-identified patent and that said Letters Patent is hereby corrected as shown below:

Title page,
Item [73], Assignee, change "Memorec Medical Molecular Research Cologne Stoffel, Gmbh" to -- Memorec Biotec Gmbh --.

Signed and Sealed this

Fifteenth Day of March, 2005

JON W. DUDAS
*Director of the United States Patent and Trademark Office*